United States Patent [19]
Ralph et al.

[11] Patent Number: 5,989,291
[45] Date of Patent: Nov. 23, 1999

[54] INTERVERTEBRAL SPACER DEVICE

[75] Inventors: James D. Ralph, Oakland; Stephen Tatar, Montvale, both of N.J.

[73] Assignee: Third Millennium Engineering, LLC, Summit, N.J.

[21] Appl. No.: 09/031,241

[22] Filed: Feb. 26, 1998

[51] Int. Cl.⁶ ........................................... A61F 2/44
[52] U.S. Cl. .............................................. 623/17; 623/16
[58] Field of Search ........................................ 623/17, 16

[56] References Cited

U.S. PATENT DOCUMENTS

| | | | |
|---|---|---|---|
| 5,458,642 | 10/1995 | Beer et al. | 623/17 |
| 5,683,465 | 11/1997 | Shinn et al. | 623/17 |
| 5,782,832 | 7/1998 | Larsen et al. | 623/17 |
| 5,824,094 | 10/1998 | Serhan et al. | 623/17 |
| 5,865,848 | 2/1999 | Baker | 623/17 |
| 5,895,428 | 4/1999 | Berry | 623/17 |

*Primary Examiner*—David H. Willse
*Assistant Examiner*—Suzette J. Jackson
*Attorney, Agent, or Firm*—Joseph P. Errico, Esq.

[57] ABSTRACT

An intervertebral spacer device having a pair of opposing plates for seating against opposing vertebral bone surfaces, separated by at least one spring mechanism. The preferred spring mechanism is a belleville washer. In a first embodiment there are two belleville washers which are oriented in opposite directions such that the narrow ends thereof are in contact with each other and the wider ends are in contact with the respective end plates. In a second embodiment there is a single belleville washer which is modified to mount onto a ball-shaped head. The lower plate of this embodiment includes a post extending upwardly from the inner surface of the plate, the post including a ball-shaped head. The modified belleville washer is lockably mounted to the head such that the wider portion of the washer seats against the upper plate.

18 Claims, 4 Drawing Sheets

INTERVERTEBRAL SPACER DEVICE

BACKGROUND OF THE INVENTION

1. Field of the Invention

This invention relates generally to a spinal implant assembly for implantation into the intervertebral space between adjacent vertebral bones to simultaneously provide stabilization and continued flexibility and proper anatomical motion.

2. Description of the Prior Art

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks thepathology under a stabilizing bridge of bone. This bone fusion limits the overall flexibility of the spinal column and artifically constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. This spring mechanism provides a strong restoring force when a compressive load is applied to the plates, and may also permit limited rotation of the two plates relative to one another. While there are a wide variety of embodiments contemplated, two embodiment families are described herein as representative of preferred types.

More particularly, with respect to the base plates, which are similar in all embodiments, as the assembly is to be positioned between the facing surfaces of adjacent vertebral bodies, and as such need to have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates must each include outwardly directed spikes which penetrate the bone surface and mechanically hold the plates in place. It is further anticipated that the plates should include a porous coating into which the bone of the vertebral body can grow. (Note that this limited fusion of the bone to the base plate does not extend across the intervertebral space.) Between the base plates, on the exterior of the device, there is included a circumferential wall which is resilient and which simply prevents vessels and tissues from entering within the interior of the device. This resilient wall may comprise a porous fabric or a semi-impermiable elastomeric material. Suitable tissue compatible materials meeting the simple mechanical requirements of flexibility and durability are prevalent in a number of medical fields including cardiovascular medicine, wherein such materials are utilized for venous and aterial wall repair, or for use with artificial valve replacements. Alternatively, suitable plastic materials are utilized in the surgical repair of gross damage to muscles and organs. Still further materials which could be utilized herein may be found in the field of orthopaedic in conjunction with ligament and tendon repair. It is anticipated that future developments in this area will produce materials which are compatible for use with this invention, the breadth of which shall not be limited by the choice of such a material.

As introduced above, the internal structure of the present invention comprises a spring member, or other equivalent subassembly which provides a restoring force when compressed. More particularly, it is desirable that the restoring forces be directed outward against the opposing plates, when a compressive load is applied to the plates. In addition, in certain select embodiments, it is necessary that the restoring force providing subassembly not substantially interfere with the rotation of the opposing plates relative to one another. In a first embodiment, the spring subassembly does not interfere with the rotation of the plates. In the second preferred embodiment, the spring subassembly prevents any rotation of the plates.

More particularly with respect to the first embodiment, in which the restoring force providing subassembly does not interfere with the rotation of the plates, the restoring force providing subassembly comprises a pair of belleville washers. Belleville washers are washers which are frustoconical in shape. Specifically, they have a radial convexity (i.e., the height of the washers is not linearly related to the radial distance, but may, for example, be parabolic in shape). The restoring force of a belleville washer is proportional to the elastic properties of the material. As a compressive load is applied to a belleville washer, the forces are directed into a hoop stress which tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition. The belleville washer is one of the strongest configurations for a spring, and is highly suitable for use as a restoring force providing subassembly for use in an intervertebral spacer element which must endure considerable cyclical loading in an active human adult. In the present invention, two belleville washers are oriented such that the two raised conical ends of the washers are facing one another. The wider ends of the washers are compressed and/or coupled to the respective inner surfaces of the base plates. A compressive load applied to the base plates causes the corresponding compression of the belleville washers, which in turn causes a restoring force to be applied to the base plates. It shall be understood that the belleville washers may rotate relative to one another without interfering with the restoring force it provides to the base plates. In this way the base plates may rotate relative to one another while maintaining a constant resilient capacity relative to the adjacent bone.

In a second and preferred embodiment of the present invention, a single modified belleville washer is utilized in conjunction with a ball-shaped post on which it is free to rotate through a range of angles (thus permitting the plates to rotate relative to one another through a corresponding range of angles). More particularly, this second embodiment comprises a pair of spaced apart base plates, one of which is simply a disc shaped member having external and internal flat faces. The other of the plates is similarly shaped, having a flat exterior surface, but further includes a short central post portion which rises out of the interior face at a nearly perpendicular angle. The top of this short post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, a modified belleville washer is mounted to this ball-shaped knob in such a way that it may rotate freely through a range of angles equivalent to the fraction of normal human spine rotation (to mimic normal disc rotation). The belleville washer of this design is modified by including an enlarged inner circumferential portion which accomodates the ball-shaped portion of the post. More particularly, the enlarged portion of the modified belleville washer includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the belleville washer, and the washer to be rotated into the proper lordotic angulation. Subsequent introduction of the set screw into the axial bore of the post locks the head in the belleville washer. Ideally the post head is locked tightly within the central volume of the modified belleville washer by the insertion of the set screw, thus preventing any rotation of the plates. This assembly provides ample spring-like performance with respect to axial compressive loads, as well as long cycle life to mimic the axial biomechanical performance of the normal human intervertebral disc.

Finally, inasmuch as the human body has a tendency to produce fibrous tissues in perceived voids, such as may be found within the interior of the present invention, and such fibrous tissues may interfere with the stable and/or predicted functioning of the device, preferred embodiments of the present invention will be filled with a highly resilient elastomeric material. The material itself should be highly biologically inert, and should not substantially interfere with the restoring forces provided by the spring-like mechanisms therein. Suitable materials may include hydrophilic monomers such as are used in contact lenses. Alternative materials include silicone jellies and collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the present invention shall not limit the breadth thereof.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
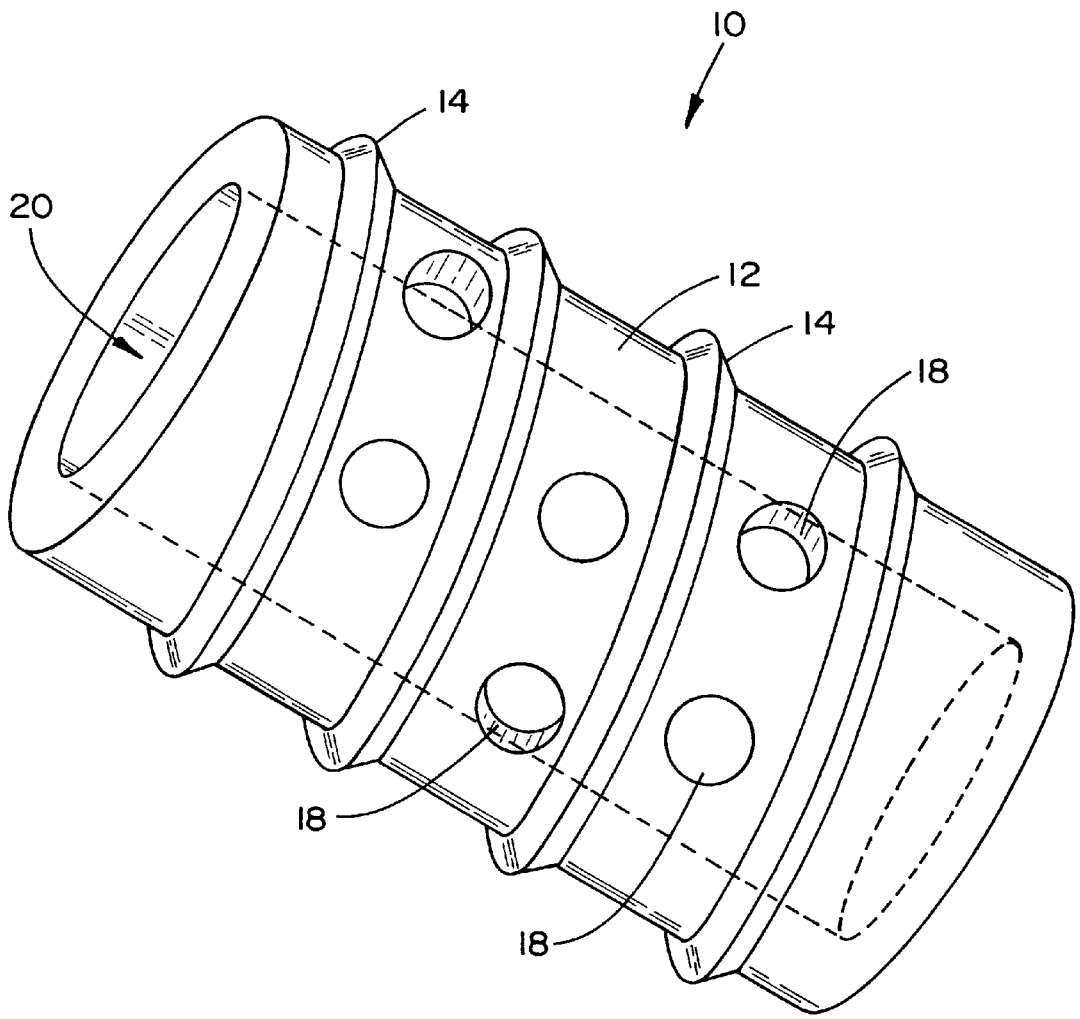
FIG. 1 is a side perspective view of an interbody fusion device of the prior art.
Figure 2:
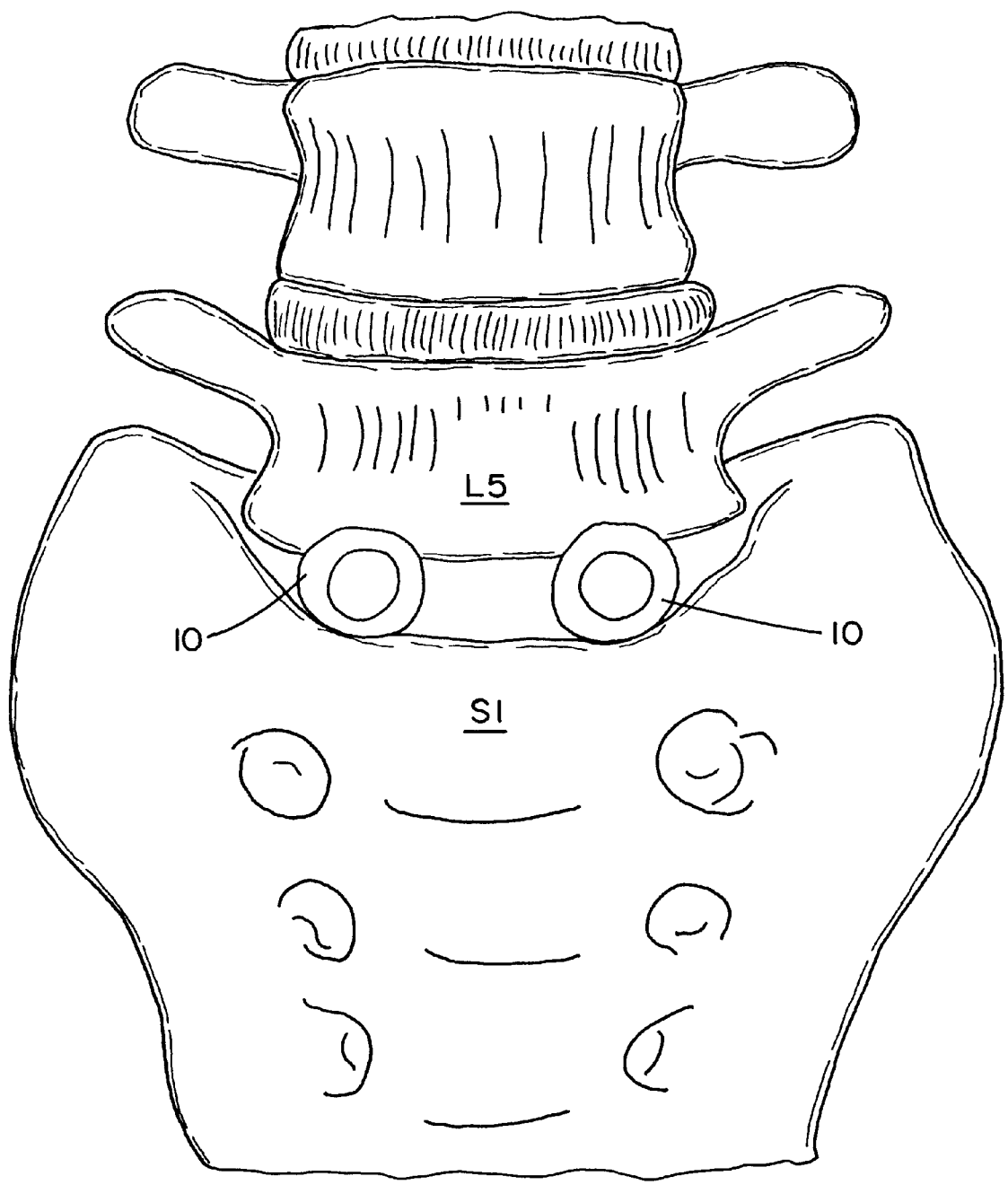
FIG. 2 is a front view of the anterior portion of the lumbo-sacral region of a human spine, into which a pair of interbody fusion devices of the type shown in FIG. 1 have been implanted.
Figure 3A:
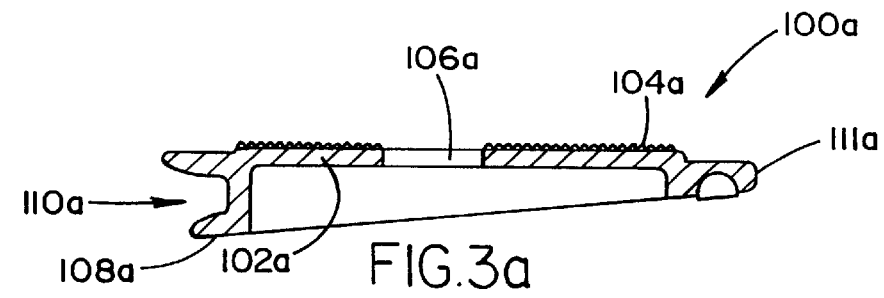
FIGS. 3a and 3b are side cross-section views of the upper and lower opposing plates of the present invention.
Figure 3B:
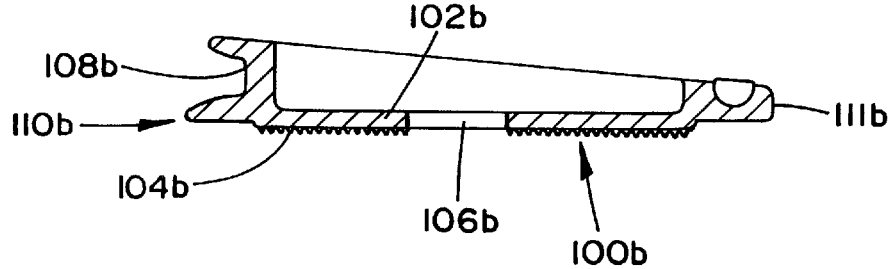

Referring now to FIGS. 3a and 3b, side cross-section views of the top and bottom plate members 100a 100b of a first embodiment of the present invention is shown. More particularly, in this embodiment, the upper and lower plates 100a, 100b are identical. As the device is designed to be positioned between the facing surfaces of adjacent vertebral bodies, the plates include substantially flat surface portions 102a, 102b which seat against the opposing bone surfaces. In addition, the plates are to mate with the bone surfaces in such a way as to not rotate relative thereto. It is, therefore, preferred that the plates should include a porous coating 104a, 104b into which the bone of the vertebral body can grow. (Note that this limited fusion of the bone to the base plate does not extend across the intervertebral space.) An additional hole 106a,106b is provided in each plate such that the interior of the device may be readily accessed if a need should arise.

The plates 100a, 100b further include a circumferential skirt comprised of an offset flange 108a, 108b. The offset corresponds to the front 110a,110b and rear 111a, 111b orientation of the overall assembly. More particularly, the offset nature of the flanges 108a, 108b is exhibited in the non-symmetric appearance of each flange as it circumscribes the corresponding plate 100a, 100b. By this it is meant that the portion of the flange 108a,108b which corresponds to the rear 111a,111b of the device is shorter than the portion corresponding to the front 110a,110b of the device.

Figure 4:
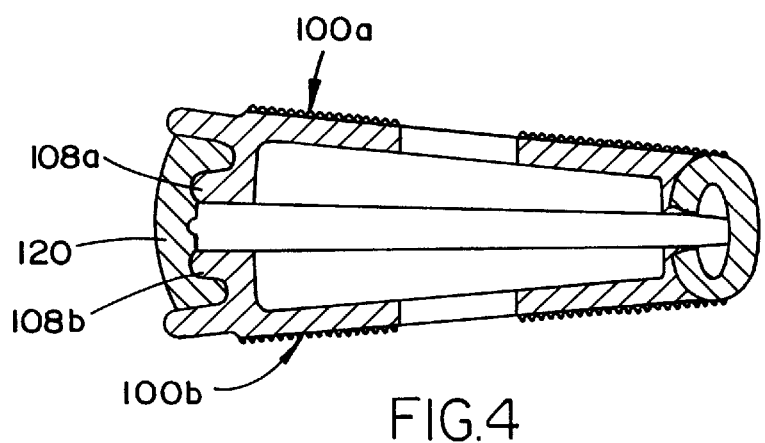
FIG. 4 is a side cross-section view of the opposing plates in association with one another, wherein an exterior skirt is included.

Referring now to FIG. 4, a partially assembled embodiment of the present invention is provided in a side cross-section view, wherein the upper and lower plates 100a, 100b illustrated in FIGS. 3a and 3b are joined by means of a circumferential wall 120. More particularly, between the base plates 100a, 100b, on the exterior of the device, there is included a circumferential wall 120 which is resilient and which is provided to prevents vessels and tissues from entering within the interior of the device. It is preferred that the resilient wall 120 comprise a porous fabric or a semi-impermiable elastomeric material. The wall 120 is further designs to couple lo the flanges 108a, 108b of the corresponding plates 100a, 100b.

Figure 5:
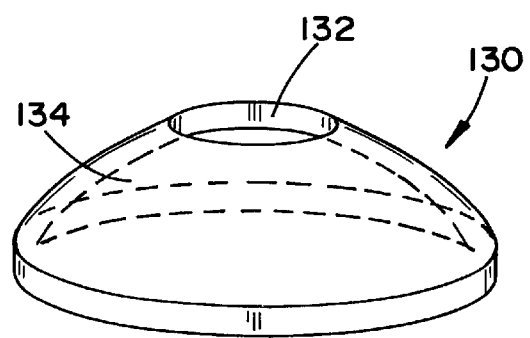
FIG. 5 is perspective view of a belleville washer of the type which is utilized in conjunction with an embodiment of the present invention.

Referring now to FIG. 5, a belleville washer 130 is provided in a perspective view. A belleville washer 130 is a restoring force providing device which comprises a circular shape, having a central opening 132, and which is frusto-conical in shape. Most belleville washers have a radial convexity 134 (i.e., the height of the washer 130 is not linearly related to the radial distance, but may, for example, be parabolic in shape). The restoring force of a belleville washer is proportional to the elastic properties of the material. As a compressive load is applied to a belleville washer, the forces are directed into a hoop stress which tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition.

Figure 6:
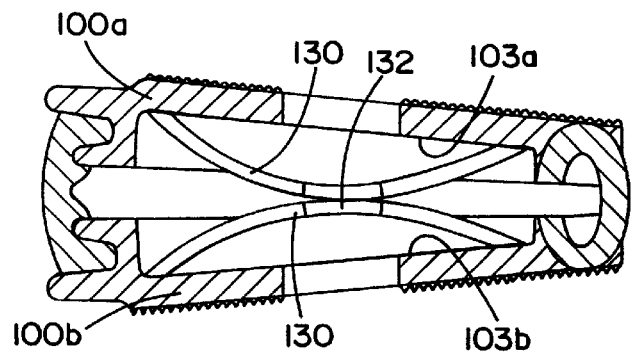
FIG. 6 is a side cross-section view of a first embodiment of the present invention which utilizes a pair of belleville washers of the type shown in FIG. 5.

Referring now to FIG. 6, the first embodiment of the present invention is provided in a side cross-section view. The embodiment comprises two belleville washers 130 which are oriented such that the two central openings 132 of the raised conical ends of the washers 130 are facing one another. The wider ends of the washers 130 are compressibly retained in the interior of the device, between the inner surfaces 103a,103b of the plates 100a,100b. As a result, compressive load applied to the plates 100a, 100b causes the corresponding compression of the belleville washers 130, which in turn causes a restoring force to be applied to the plates 100a,100b.

Figure 7:
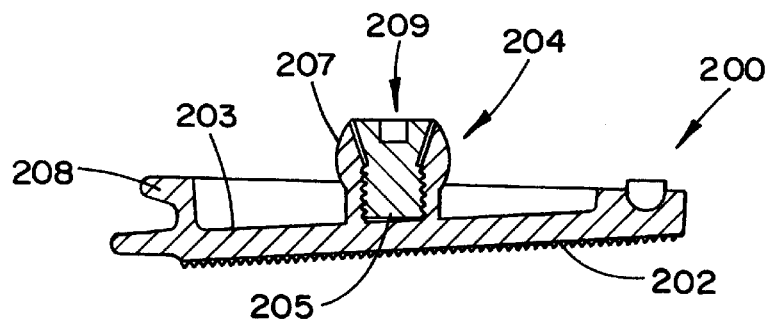
FIG. 7 is a side cross-section view of the lower opposing plate of the present invention; which is utilized in another embodiment.

Referring now to FIG. 7, an alternative lower plate 200 is shown in a side cross-section view. In this alternative embodiment, the plate 200 is similarly shaped to the plates described above, i.e., having a flat exterior surface 202 and a circumferential flange 208, but further includes a short central post member 204 which rises out of the interior face 203 at a nearly perpendicular angle. The top of this short post member 204 includes a ball-shaped head 207. The head 207 includes a central threaded axial bore 209 which extends down the post 204. This threaded bore 209 is designed to receive a small set screw 205. Prior to the insertion of the set screw 205, the ball-shaped head 207 of the post 204 can deflect radially inward (so that the ball-shaped head contracts). The insertion of the set screw 205 eliminates the capacity for this deflection.

Figure 8:
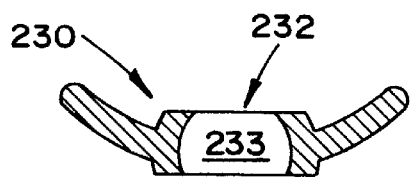
FIG. 8 is a side cross-section view of a modified belleville washer of the type used in conjunction with another embodiment of the present invention.

Referring now to FIG. 8, a modified belleville washer 230 is shown in a side cross-section view. This belleville washer design is similar to the belleville washer described above with respect to FIG. 5, with the additional feature of having an enlarged central opening 232. This central opening 232 includes a curvate volume 233 for receiving therein the ball-shaped head 207 of the post 204 of the lower plate 200 described above. More particularly, the curvate volume 233 has a substantially constant radius of curvature which is also substantially equivalent to the radius of the ball-shaped head 207 of the post 204.

Figure 9:
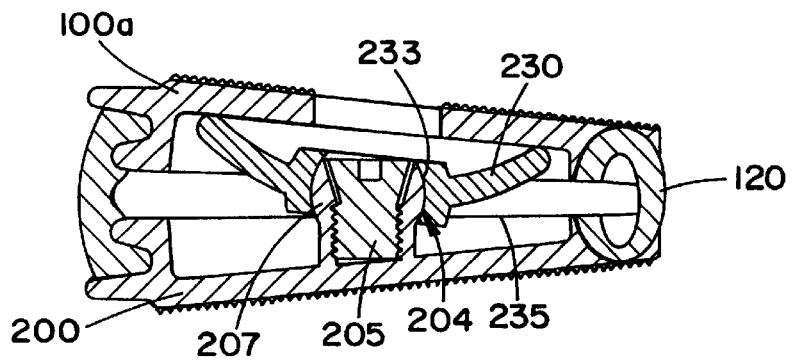
FIG. 9 is a side cross-section view of a first embodiment of the present invention which utilizes a single modified belleville washer of the type shown in FIG. 8.

Referring also to FIG. 9, in which the fully assembled second embodiment of the present invention is shown, the combination and assembly of this embodiment is now provided. The deflectability of the ball-shaped head 207 of the post 204, prior to the insertion of the set screw 205, permits the head 207 to be inserted into the interior volume 233 at the center of the modified belleville washer 230, and the washer 230 to be rotated into the desired angulation. Subsequent introduction of the set screw 205 into the axial bore 209 of the post 204 locks the head 207 in the belleville washer 230. Ideally the post head 207 is locked tightly within the central volume 233 of the modified belleville washer 230 by the insertion of the set screw 205, thus preventing any rotation of the plates 100a,200.

Inasmuch as the human body has a tendency to produce fibrous tissues in perceived voids, such as may be found within the interior of the present invention, and such fibrous tissues may interfere with the stable and/or predicted functioning of the device, preferred embodiments of the present invention will be filled with a highly resilient and biologically inert elastomeric material 235. Suitable materials may include hydrophilic monomers such as are used in contact lenses. Alternative materials include silicone jellies and collagens such as have been used in cosmetic applications.

While there has been described and illustrated embodiments of an intervertebral spacer device, it will be apparent to those skilled in the art that variations and modifications are possible without deviating from the broad spirit and principle of the present invention. The present invention shall, therefore, be limited solely by the scope of the claims appended hereto.

We claim:

1. An intervertebral spacer device comprising first and second plate members, each having plate surfaces thereof, said plates being disposed in a spaced apart relationship such that inner ones of said plate surfaces oppose one another, and external ones of said plate surfaces face in opposite directions; and
    at least one restoring force providing element disposed between the inner surfaces of said first and second plate members, and disposed such that a compressive load applied to the external faces of said plates is counteracted by said at least one restoring force providing element, said at least one restoring force providing element including at least one belleville washer having a narrow end and a wide end.

2. The device as set forth in claim 1, further comprising a flexible circumferential skirt disposed about and between the lateral perimeters of said first and second plate members, therein defining an interior volume of said device in which said at least one restoring force providing element is contained.

3. The device as set forth in claim 2, wherein said flexible circumferential skirt comprises a resilient material.

4. The device as set forth in claim 2, wherein said flexible circumferential skirt is porous.

5. The device as set forth in claim 1, wherein said at least one belleville washer comprises a pair of belleville washers.

6. The device as set forth in claim 5, wherein said pair of belleville washers are oriented such that said narrow ends are in contact with one another and said wide ends are in contact with respective inner surfaces of said first and second plates.

7. The device as set forth in claim 1, wherein at least one of said external surfaces of said first and second plates comprises a porous coating.

8. The device as set forth in claim 1, wherein said second plate further comprises a post structure rising off the inner surface thereof, and which post structure includes a ball-shaped head.

9. The device as set forth in claim 8, wherein said post further includes a threaded bore which extends axially from said ball-shaped head downwardly, and which bore receives therein a threaded set screw such that prior to insertion of the set screw therein, said bore permits the ball-shaped head to compress radially inwardly, and such that after the insertion of said set screw said ball-shaped head is not readily radially compressible.

10. The device as set forth in claim 8, wherein said at least one belleville washer further comprises a central opening which includes a curvate volume for receiving and holding therein said ball-shaped head.

11. The device as set forth in claim 2, wherein at least a portion of said interior volume defined by said flexible circumferential skirt includes the inclusion of a filling material for preventing fibrous tissue ingrowth.

12. The device as set forth in claim 11, wherein said filling material is elastomeric.

13. An intervertebral spacer device comprising
    first and second plate members, each having plate surfaces thereof, said plates being disposed in a spaced apart relationship such that inner ones of said plate surfaces oppose one another, and external ones of said plate surfaces face in opposite directions, said first and second plate members further including circumferential flange elements extending outwardly from said inner surfaces;
    a flexible circumferential skirt disposed about and between the lateral perimeters of said first and second plate members, coupled to said circumferential flange elements of each plate member, therein defining an interior volume;
    a pair of belleville washers, each having narrow and wide ends thereof, disposed such that said narrow ends thereof are in contact with one another and the wide ends of each is in contact with the corresponding inner surface of the corresponding plate, said wide end being retained within the circumferential flange of the corresponding plate, whereby said belleville washers are disposed such that a compressive load applied to the external faces of said plates is counteracted by the washers.

14. The device as set forth in claim 13 wherein said flexible circumferential skirt comprises a resilient material.

15. The device as set forth in claim 13 wherein said flexible circumferential skirt is porous.

16. The device as set forth in claim 13, wherein at least one of said external surfaces of said first and second plates comprises a porous coating.

17. An intervertebral spacer device comprising
    first and second plate members, each having plate surfaces thereof; said plates being disposed in a spaced apart relationship such that inner ones of said plate surfaces oppose one another, and external ones of said plate surfaces face in opposite directions, said first and second plate members further including circumferential flange elements extending outwardly from said inner surfaces;

said second plate member further including a post structure rising off the inner surface thereof, and which post structure includes a ball-shaped head;

a flexible circumferential skirt disposed about and between the lateral perimeters of said first and second plate members, coupled to said circumferential flange elements of each plate member, therein defining an interior volume;

a belleville washer, having narrow and wide ends thereof, said narrow end including a central opening which includes a curvate volume for receiving and holding therein said ball-shaped head, wherein said wide end of said washer is in contact with the corresponding inner surface of the first plate, said wide end being retained within the circumferential flange of the corresponding plate, whereby said belleville washer is disposed such that a compressive load applied to the external faces of said plates is counteracted by the restoring force of said washer.

18. The device as set forth in claim 17, wherein said post further comprises a threaded bore which extends axially from said ball-shaped head downwardly, and which bore receives therein a threaded set screw such that prior to insertion of the set screw therein, said bore permits the ball-shaped head to compress radially inwardly, and such that after the insertion of said, set screw said ball-shaped head is not readily radially compressible.

* * * * *